(12) United States Patent
Juhasz et al.

(10) Patent No.: US 7,892,226 B2
(45) Date of Patent: Feb. 22, 2011

(54) METHOD OF CORNEAL SURGERY BY LASER INCISING A CONTOURED CORNEAL FLAP

(75) Inventors: Tibor Juhasz, Irvine, CA (US); J. Randy Alexander, Newport Beach, CA (US)

(73) Assignee: AMO Development, LLC., Santa Ana, CA (US)

( * ) Notice: Subject to any disclaimer, the term of this patent is extended or adjusted under 35 U.S.C. 154(b) by 1361 days.

(21) Appl. No.: 11/368,960

(22) Filed: Mar. 6, 2006

(65) Prior Publication Data

US 2006/0155265 A1     Jul. 13, 2006

Related U.S. Application Data

(63) Continuation of application No. 09/536,861, filed on Mar. 27, 2000, now abandoned, which is a continuation-in-part of application No. 08/725,070, filed on Oct. 2, 1996, now Pat. No. 6,110,166, which is a continuation-in-part of application No. 08/407,508, filed on Mar. 20, 1995, now abandoned.

(51) Int. Cl.
*A61F 9/008* (2006.01)
(52) U.S. Cl. ............................. 606/5; 606/4; 128/898
(58) Field of Classification Search ............ 606/4, 606/5; 128/898
See application file for complete search history.

(56) References Cited

U.S. PATENT DOCUMENTS

| | | | |
|---|---|---|---|
| 3,769,963 A | 11/1973 | Goldman | |
| 4,309,998 A | 1/1982 | Aron nee Rosa | |
| 4,391,275 A | 7/1983 | Fankhauser et al. | |
| 4,538,608 A | 9/1985 | L'Esperance, Jr. | |
| 4,580,559 A | 4/1986 | L'Esperance | |
| 4,601,288 A | 7/1986 | Myers | |
| 4,633,866 A | 1/1987 | Peyman | |
| 4,665,913 A | 5/1987 | L'Esperance, Jr. | |
| 4,669,466 A | 6/1987 | L'Esperance | |

(Continued)

FOREIGN PATENT DOCUMENTS

WO     WO 93/08878     5/1993

(Continued)

OTHER PUBLICATIONS

Ratkay-Traub l et al. Ultra-short pulse (Femtosecond) laser surgery, Initial use in LASIK flap creation. Ophthalmology Clinics of North America 2001; 14(2):347-55.

(Continued)

*Primary Examiner*—Henry M Johnson, III
*Assistant Examiner*—Jeffrey B Lipitz

(57) ABSTRACT

A method of corneal laser surgery is disclosed. A first periphery is defined at an anterior surface of the cornea. This first periphery bounds a first planar area. A second periphery is defined within stromal tissue of the cornea. This second periphery bounds a second planar area. The second planar area is sized differently than the first planar area. A layer of stromal tissue which is bounded by the second periphery is subsequently incised. Stromal tissue between substantial portions of the first periphery and the second periphery is also incised, such that at least some corneal tissue disposed between the first and second peripheries remains connected to corneal tissue outside of the first and second peripheries.

15 Claims, 4 Drawing Sheets

U.S. PATENT DOCUMENTS

| | | | |
|---|---|---|---|
| 4,718,418 A | 1/1988 | L'Esperance, Jr. | |
| 4,721,379 A | 1/1988 | L'Esperance | |
| 4,732,148 A | 3/1988 | L'Esperance | |
| 4,764,930 A | 8/1988 | Bille et al. | |
| 4,770,172 A | 9/1988 | L'Esperance | |
| 4,773,414 A | 9/1988 | L'Esperance, Jr. | |
| 4,842,599 A * | 6/1989 | Bronstein | 623/5.15 |
| 4,887,592 A | 12/1989 | Loertscher | |
| 4,903,695 A | 2/1990 | Warner et al. | |
| 4,907,586 A | 3/1990 | Bille et al. | |
| 4,941,093 A | 7/1990 | Marshall | |
| 4,988,348 A | 1/1991 | Bille | |
| 5,049,147 A | 9/1991 | Danon | |
| 5,108,428 A | 4/1992 | Capecchi et al. | |
| 5,439,462 A | 8/1995 | Bille et al. | |
| 5,549,632 A | 8/1996 | Lai | |
| 5,722,971 A * | 3/1998 | Peyman | 606/5 |
| 5,984,916 A | 11/1999 | Lai | |
| 5,984,961 A * | 11/1999 | Macoul | 623/5.12 |
| 5,993,438 A | 11/1999 | Juhasz et al. | |
| 6,090,100 A | 7/2000 | Hohla | |
| 6,099,522 A | 8/2000 | Knopp et al. | |
| 6,110,166 A | 8/2000 | Juhasz | |
| 6,210,401 B1 | 4/2001 | Lai | |
| 6,325,792 B1 | 12/2001 | Swinger et al. | |
| 6,331,117 B1 | 12/2001 | Brundage | |
| 6,344,040 B1 | 2/2002 | Juhasz et al. | |
| 6,350,272 B1 * | 2/2002 | Kawesch | 606/166 |
| 6,451,006 B1 | 9/2002 | Bille | |
| 6,554,424 B1 * | 4/2003 | Miller et al. | 351/160 R |
| 6,641,577 B2 | 11/2003 | Bille | |
| 2002/0087150 A1 | 7/2002 | Juhasz et al. | |
| 2003/0073983 A1 | 4/2003 | Bille | |

FOREIGN PATENT DOCUMENTS

| | | |
|---|---|---|
| WO | WO 94/09849 | 5/1994 |
| WO | WO 98/14244 A1 | 4/1998 |

OTHER PUBLICATIONS

Ito M. et al. Picosecond laser in situ keratomileusis with a 1053-nm Nd:YLF laser. Journal of Refractive Surgery 1996; 12:721-728.

Niemz MH et al. Intrastromal ablations for refractive corneal surgery using picosecond infrared laser pulses. Lasers and Light in Ophthalmology 1993; 5(3): 149-55.

Juhasz T et al. Corneal refractive surgery with femtosecond lasers. Journal of Selected Topics in Quantum Electronics 1999; 5(4): 902-910.

Niemz MH et al. Plasma-mediated ablation of corneal tissue at 1053 nm using a Nd:YLF oscillator regenerative amplifier laser. Laser in Surgery and Medicine 1991; 11;426-31.

Remmel RM et al. Instrastromal tissue removal using an infrared picosecond Nd:YLF ophthalmic laser operating at 1053 nm. Laser sand Light in Ophthalmology 1992; 4(3/4): 169-73.

Kautek et al, "Femtosecond-Pulse Laser Ablation of Human Corneas," Applied Physics A58, pp. 513-518 91994).

Ajit P. Joglekar et al. Optics at critical intensity: Applications to nanomorphing, PNAS, 5856-5861, Apr. 20, 2004, vol. 101, No. 16.

A.P. Joglekar et al., A study of the deterministic character of optical damage by femtosecond laser pulses and applications to nanomachining, Appl. Phys. B 77, 25-30 (2003).

Imola Ratkay-Traub et al., First Clinical Results With the Femtosecond Neodynium-glass Laser in Refractive Surgery, Journal of Refractive Surgery, 94-103, vol. 19, Mar./Apr. 2003.

Picosecond Laser in situ Keratomilensis with a 1053-nm Nd:YLD Laser by Ito et al. J. of Refract. Surg.; vol. 12 Sep. 1996, pp. 721-728.

Tadeusz Krawawicz, Lamellar corneal Stromectomy, pp. 828-833.

John Marshall et al., Photoablative reprofiling of the cornea using an Excimer Laser; Photorefractive Keratectomy, Lasers in Ophtalmology, vol. 1, No. 1, pp. 21-48, 1986.

Supplemental Search Report of European Application No. EP08005039, mailed Jun. 23, 2008, 4 pages total.

\* cited by examiner

METHOD OF CORNEAL SURGERY BY LASER INCISING A CONTOURED CORNEAL FLAP

Priority is claimed as a continuation to U.S. Ser. No. 09/536,861, filed Mar. 27, 2000, now abandoned, which claims priority as a continuation-in-part to U.S. Pat. No. 6,110,166, issued on Aug. 29, 2000 from application Ser. No. 08/725,070, filed Oct. 2, 1996, which claims priority as a continuation-in-part to U.S. application Ser. No. 08/407,508, filed Mar. 20, 1995, now abandoned. The disclosures of each of the aforementioned priority documents is incorporated herein by reference in their entirety.

FIELD OF THE INVENTION

The present invention pertains generally to ophthalmic surgery which is useful for correcting vision deficiencies. More particularly, the present invention pertains to methods which surgically correct the vision of a patient by removing portions of the stroma to reshape the cornea. The present invention is particularly, but not exclusively useful as a method for correcting the vision of a patient by lifting a contoured corneal flap created by a laser beam to expose a bed of stromal tissue, photoaltering the exposed bed of stromal tissue in a predetermined manner and subsequently repositioning the flap.

BACKGROUND OF THE INVENTION

Vision impairments such as myopia (i.e. near-sightedness), hyperopia (i.e. far-sightedness) and astigmatism can be corrected using eyeglasses or contact lenses. Alternatively, the cornea of the eye can be reshaped surgically to provide the needed optical correction. For example, it is known that if part of the cornea is removed, the pressure exerted on the cornea by the aqueous humor in the anterior chamber of the eye will act to close the void created in the cornea, resulting in a reshaped cornea. By properly selecting the size, shape and location of a corneal void, the desired shape, and hence optical properties of the cornea can be obtained.

One procedure employed to reshape the cornea is to remove portions of the anterior portion of the cornea. For example, see U.S. Pat. No. 4,665,913 which issued to L'Esperance for an invention entitled "Method for Ophthalmological Surgery," and U.S. Pat. No. 4,669,466 which issued to L'Esperance for an invention entitled "Method and Apparatus for Analysis and Correction of Abnormal Refractive Errors of the Eye." Another procedure used to reshape the cornea removes and reshapes subsurface tissue such as stromal tissue. As an example of such a procedure, U.S. Pat. No. 4,907,586, which issued to Bille et al. for an invention entitled "Method for Reshaping the Eye," discloses an intrastromal photoalteration technique for reshaping the cornea. Importantly for the purposes of the present invention, the above cited Bille patent discloses the use of a pulsed laser beam for photoalteration of intrastromal tissue. As disclosed by Bille, the pulsed laser beam penetrates corneal tissue and is focused at a point below the surface of the cornea to photoalter stromal tissue at the focal point. The ability to reach a subsurface location without necessarily providing a physical pathway allows for great flexibility in corneal reshapings and can reduce the total amount of tissue disruption required for a particular corneal reshaping. Further, as the prescribed corneal void shape becomes more complex and precise, the need to access subsurface tissue without a physical pathway becomes more important.

Recently developed so-called LASIK procedures incise the anterior portion of the cornea using a microkerotome to create a flap. It should be recognized that a microkeratome is a mechanical device that uses an automated blade to create a flap. Once created, the flap can be temporarily lifted for photoalteration of the exposed stroma. This procedure, like the procedure disclosed in Bille et al. '586, has as its objective the removal of only stromal tissue with the consequent preservation of anterior corneal tissue. As discussed above, the LASIK procedure relies on a physically prepared pathway, and hence is limited to simple flap configurations. In contrast with the simple flap configurations which can be prepared using a microkerotome, the procedure of the present invention recognizes that a pulsed laser beam can be focused below the surface to create complex flap designs.

In light of the above, it is an object of the present invention to provide a method for corneal laser surgery that corrects the refractive characteristics of the cornea by removing only stromal tissue and minimizes the total amount of tissue undergoing photoalteration. Another object of the present invention is to provide a method for corneal laser surgery which creates a corneal flap having a complex peripheral edge such as a peripheral edge which can be repositioned in an interlocking relationship with undisturbed corneal tissue to hold the corneal flap in place during subsequent healing, or a peripheral edge that incorporates a tab to assist in lifting and repositioning the corneal flap. Still another object of the present invention is to provide a method for corneal laser surgery which creates a corneal flap that can be lifted to expose and then photoalter a bed of stromal tissue that has a complex shape, such as a convex, concave or irregularly shaped bed. Yet another object of the present invention is to provide a method for corneal laser surgery which is relatively easy to practice and comparatively cost effective.

SUMMARY OF THE PREFERRED EMBODIMENTS

In accordance with the present invention, a method for corneal laser surgery includes the step of first prescribing the size, shape and location of stromal tissue which needs to be removed in order to correct the vision deficiency of a patient. This volume of stromal tissue which is to be removed is generally in the form of a lentoid that is defined by an anterior surface and a posterior surface and may contain an annular surface. In general, the surfaces of the lentoid can be either plane, convex, concave or irregular. In the method of the present invention, a contoured corneal flap having an interior surface and a peripheral edge is created wherein the interior surface of the flap is shaped to conform to the anterior surface of the prescribed lentoid.

To create the contoured corneal flap, a pulsed laser beam is focused to a preselected start point within the stromal tissue. In accordance with preplanned procedures, the focal point will be located on the intended interior surface of the flap. The focal point is then moved within the stromal tissue to cut (photoalter) a layer of tissue having the desired contour of the interior surface of the flap (and hence the anterior surface of the prescribed lentoid). Next, the focal point is moved within the cornea to create a peripheral edge for the flap. In this case, the peripheral edge of the flap is a surface that extends from the perimeter of the interior surface of the flap to the anterior surface of the cornea. In the preferred embodiment of the present invention, the peripheral edge may incorporate features which allow the flap to interlock with the cornea when the flap is repositioned. Further, the peripheral edge of the flap may be formed with a tab to assist in lifting and repositioning the flap. Still further, the border of the anterior surface of the flap and the perimeter of the interior surface of the flap, both of which lie on the peripheral edge, are generally curvilinear, but are not closed curves. Rather, the flap is formed with a hinge of corneal tissue which allows for flap rotation about the hinge during lifting and repositioning of the flap relative to the cornea.

Once created, the contoured corneal flap can be lifted to expose a bed of intrastromal tissue. Next, an excimer laser can be used to photoalter the bed of intrastromal tissue in a predetermined manner, thus creating the posterior surface of the prescribed lentoid. Finally, the flap having a contoured inner surface that defines the anterior surface of the lentoid, can be repositioned over the newly created void and allowed to heal. The result is a reshaped cornea that effectively corrects a patient's vision deficiency. As envisioned for the present invention, lasers may be used for plasma mediated tissue ablation (generally superficial tissue) and for plasma mediated tissue disruption (generally internal bulk tissue). Accordingly, the term photoalteration will be used herein to indicate an operation wherein there may be either plasma mediated tissue ablation or plasma mediated tissue disruption.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
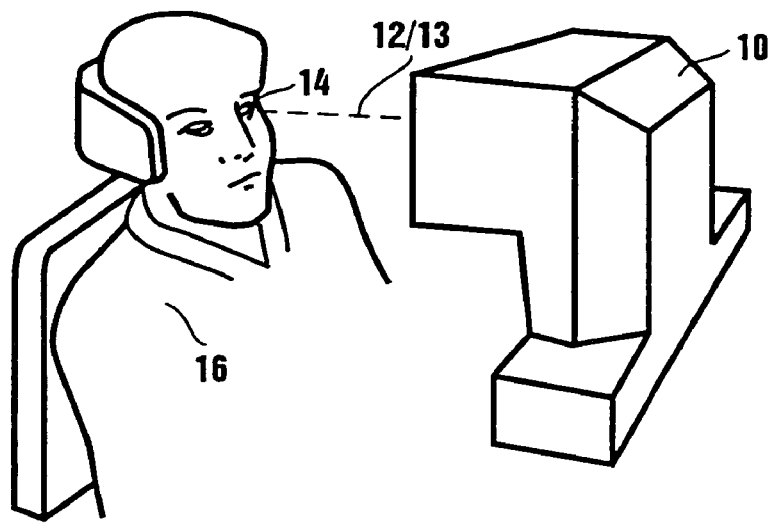
FIG. 1 is a perspective view of a patient being treated with a pulsed/excimer laser in accordance with the method of the present invention.

Referring initially to FIG. 1, an apparatus 10 for alternately generating either a pulsed laser beam 12 or an excimer laser beam 13 is shown. As hereinafter disclosed in the specification and in FIG. 1, the combined numerals 12/13 will refer respectively to either the pulsed laser beam 12 or the excimer laser beam 13. As contemplated for the present invention, the apparatus 10 will use both laser beams 12/13. Specifically, a pulsed laser beam 12 will first be used to create a flap of corneal tissue and the excimer laser beam 13 will then be used to remove corneal tissue below the flap. It will be appreciated by the skilled artisan that in lieu of an excimer laser, a pulsed infrared laser beam or a visible pulsed laser beam may be used to remove corneal tissue below the flap.

In detail, FIG. 1 shows the pulsed laser beam 12 being directed onto the eye 14 of a patient 16. For purposes of the present invention, a pulsed laser beam 12 preferably has the physical characteristics similar to those of the pulsed laser beams generated by a laser system as disclosed and claimed in U.S. Pat. No. 4,764,930, which issued to Josef F. Bille et al. for an invention entitled "Multiwavelength Laser Source." Furthermore, the present invention contemplates the use of a pulsed laser beam 12 which has pulses with durations as long as a few nanoseconds or as short as only a few femtoseconds. The pulsed laser beam 12 has a fluence of less than 100 joules per square centimeter. Also, as indicated above, the apparatus 10 will generate, a second type of laser beam; namely, an excimer laser beam 13.

Figure 2:
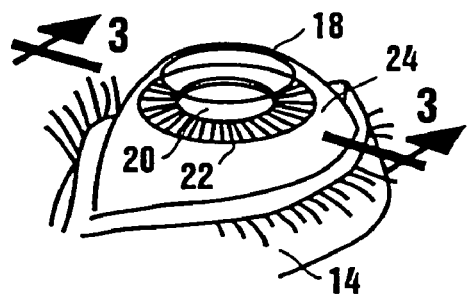
FIG. 2 is a perspective view of an eye.
Figure 3:
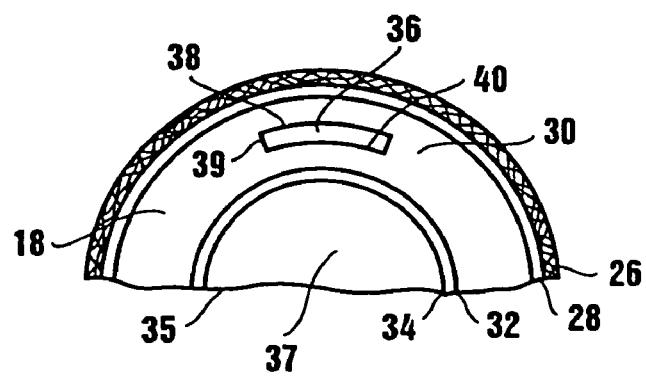
FIG. 3 is a cross sectional view of a portion of the cornea of the eye as seen along the line 3-3 in FIG. 2 showing the anatomical layers of the cornea and a representative lentoid.

FIG. 2 shows the anatomical structure of the human eye 14 including the cornea 18, the pupil 20, the iris 22, and the sclera 24. In FIG. 3 it can be seen that the cornea 18 includes five anatomically definable layers of tissue. Going in a direction from anterior to posterior in FIG. 3, the tissue layers of the cornea 18 are: the epithelium 26, Bowman's membrane 28, the stroma 30, Decemet's membrane 32 and the endothelium 34. Of these, the stroma 30 is of most importance for the present invention as it contains the only tissue which is to be removed for correction of the patient's vision. Also shown in FIG. 3, the anterior chamber 35 is a cavity filled with aqueous humor 37. The pressure exerted by in the aqueous humor 37 maintains the shape of the cornea 18.

As indicated above, it is known that the correction of myopic, hyperopic and astigmatic conditions can be accomplished by the removal of a predetermined volume of stromal tissue 30. Further, the particular volume of stromal tissue 30 to be removed for the prescribed optical correction will depend on the amount and type of correction required and will generally be a lens shaped volume (a lentoid) 36. An example of a lentoid volume 36 is shown in cross-section in FIG. 3. As shown, it is to also be appreciated that the lentoid volume 36 will be defined by an anterior surface 38, a posterior surface 40 and may have a annular surface 39.

Figure 4:
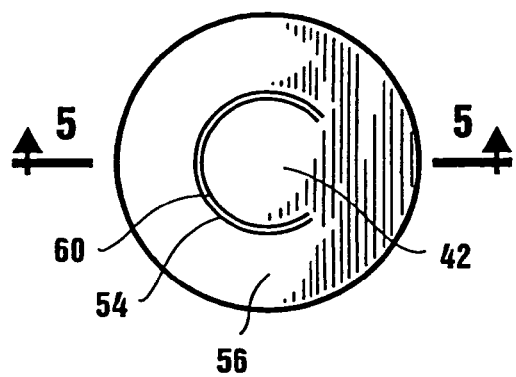
FIG. 4 is a plan view of the cornea after the incision of a flap.

In accordance with the methods of the present invention, access to the prescribed lentoid volume 36 is accomplished by using a pulsed laser beam 12 to create a contoured corneal flap 42. By cross-referencing FIGS. 4, 5A and 5B, it can be seen that the contoured flap 42 has an interior surface 44 and a peripheral edge 46. A pulsed laser beam 12 is used to create the contoured flap 42 by focusing the pulsed laser beam 12 at a point within the stromal tissue 30 and moving the focal point of the pulsed laser beam 12 within the stromal tissue 30 to cut a subsurface layer 48. Layer 48 is an interface between the interior surface 44 of flap 42 and the bed 50 of stromal tissue 30, and as such, layer 48 has a shape conforming to the prescribed shape of the interior surface 44 of the flap 42.

Next, the peripheral edge 46 for the flap 42 is created. To create the peripheral edge 46, the pulsed laser beam 12 is focused at a point within the stromal tissue 30 and on the boundary 52 of the bed 50. Then, the focal point of the pulsed laser beam 12 is moved within the stromal 30 to cut a layer 54. Layer 54 extends from the boundary 52 of bed 50 to the anterior surface 56 of the cornea 18. Layer 54 is an interface between the peripheral edge 46 of the flap 42 and the wall 58 that surrounds the bed 50. The points where the peripheral edge 46 of the flap 42 intersects the anterior surface 56 of the cornea 18 is the anterior border 60, and is shown in both FIG. 4 and FIG. 5B. Both the anterior border 60 and the boundary 52 of bed 50 may be curvilinear, but are not necessarily closed curves. Rather, in the preferred embodiment of the present invention, both the boundary 52, and the anterior border 60 terminate within the stroma 30 to create a hinge 62 of stromal tissue 30 for flap 42. Hinge 62 allows the flap 42 to be lifted while continuing to be attached to the remaining cornea 18.

Figure 5A:
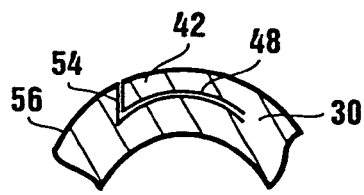
FIG. 5A is a cross-sectional view of a cornea as seen along the line 5-5 in FIG. 4, showing a flap incision for a flap having a concave interior surface.
Figure 5B:
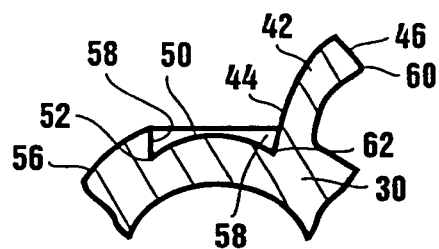
FIG. 5B is a cross-sectional view of a cornea as in FIG. 5A, showing the cornea after the incision and lifting of a flap having a concave interior surface.
Figure 5C:
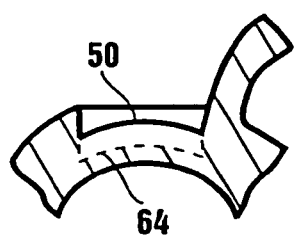
FIG. 5C is a cross-sectional view of a cornea as in FIG. 5B showing the cornea prior to photoalteration of the exposed bed, and showing the posterior and annular surfaces of the lentoid in phantom.
Figure 5D:
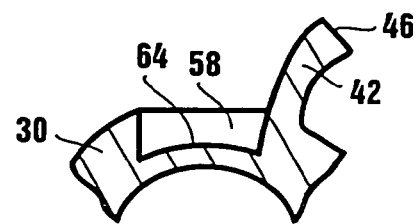
FIG. 5D is a cross-sectional view of a cornea as in FIG. 5C showing the cornea after photoalteration of the exposed bed of stromal tissue.
Figure 5E:
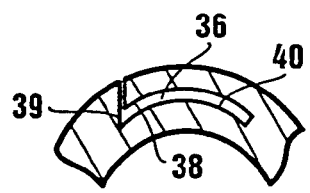
FIG. 5E is a cross-sectional view of a cornea as in FIG. 5D showing the cornea after the removal of a lentoid of stromal tissue from the exposed bed of stromal tissue by photoalteration, and replacement of the flap.

Once the flap 42 is created, the flap 42 can be lifted by rotating the flap 42 about the hinge 62 to expose the bed 50 of stromal tissue 30. The contour of the exposed bed 50 as well as the contour of the interior surface 44 of the flap 42 will conform to the layer 48 cut into the stromal tissue 30 by the pulsed laser beam 12. As shown in FIGS. 5C and 5D, after the flap 42 has been lifted and the bed 50 of stromal tissue 30 is exposed, a pulsed laser beam 12 or an excimer laser beam 13 can be used to photoalter a portion or all of the bed 50 in a predetermined manner until the posterior bed surface 64 of stromal tissue 30 is reached. The shape of the posterior bed 64 can be selectively contoured using the laser beam 12,13 to conform to the prescribed shape of the posterior surface 40 of the prescribed lentoid 36, as shown in FIG. 5E. As indicated earlier, lasers may be used for plasma mediated tissue ablation (generally superficial tissue) and for plasma mediated tissue disruption (generally internal bulk tissue). Accordingly, the term photoalteration will be used herein to indicate an operation wherein there may be either plasma mediated tissue ablation or plasma mediated tissue disruption.

As further shown by cross-referencing FIGS. 5D and 5E, after the photoalteration of the prescribed lentoid 36 volume by either an excimer laser beam 13 or a pulsed laser beam 12 is complete, the contoured flap 42 can be reengaged with the cornea 18 into a position covering the lentoid 36. In particular, the flap 42 can be rotated about the hinge 62 until the peripheral edge 46 of the flap 42 is positioned into contact with a portion of the wall 58. When the flap 42 is properly repositioned over the lentoid 36, the anterior surface 56 of the cornea 18 will be smooth and continuous across the anterior border 60 from the flap 42 to the remaining portion of the cornea 18. After repositioning, the flap 42 will heal in place, and this healing will result in a continuous tissue between the peripheral edge 46 of the flap 42 and a portion of the wall 58 of the cornea 18.

Figure 5F:
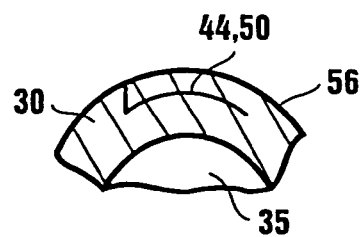
FIG. 5F is a cross-sectional view of a cornea as in FIG. 5E showing the reshaped cornea after removal of a lentoid of stromal tissue.

FIG. 5E shows the cornea 18 after the flap 42 has been repositioned, and shows an example of a lentoid 36 having an anterior surface 38, an annular surface 39 and a posterior surface 40. Further, FIG. 5F shows the reshaped cornea 18 which results after the methods of the present invention. As discussed above, after a prescribed lentoid 36 of stromal tissue 30 has been removed and the flap 42 repositioned over the lentoid 36, the pressure exerted by the aqueous humor 37 in the anterior chamber 35 will cause the cornea 18 to close the lentoid 36 volume and hence reshape the cornea 18. In particular, the pressure exerted by the aqueous humor 37 will push the posterior bed 64 into contact with the interior surface 44 of the repositioned flap 42, where the two surfaces will subsequently heal together and become continuous stromal tissue 30. By comparing FIG. 5A with FIG. 5F, it can be seen that the curvature of the anterior surface 56 of the reshaped cornea 18 (FIG. 5F) differs from the curvature of the anterior surface 56 of the initial cornea 18 (FIG. 5A).

As can be expected, the lentoid 36 shape shown in FIGS. 5A-5F is only one of the many possible lentoid 36 shapes that can be prescribed and thereafter created by the methods of the present invention. In particular, the example lentoid 36 shape as shown in FIGS. 5A-5F has a convex anterior surface 38, a concave posterior surface 40 and an annular surface 39 connecting the anterior 38 and posterior 40 surfaces. As shown, the contour of the convex anterior surface 38 does not necessarily have the same curvature as the anterior surface 56 of the cornea 18. Rather, the points on the layer 48 cut by the pulsed laser beam 12 are located at variable distances from corresponding points on the anterior surface 56 of the cornea 18. Although not required by the method of the present invention, the lentoid 36 may have anterior 38 and posterior 40 lentoid surfaces that have the same approximate curvature, such as the lentoid 36 shown in FIGS. 5A-5F. When this type of lentoid 36 is prescribed, it can be conveniently created using an excimer laser 13 configured to photoalter the exposed bed 50 of stromal tissue 30 to a uniform depth.

Figure 6A:
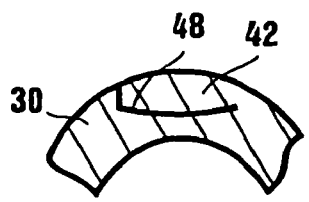
FIG. 6A is a cross-sectional view of a cornea as in FIG. 5A showing the cornea after the incision of a flap having a convex interior surface.
Figure 6B:
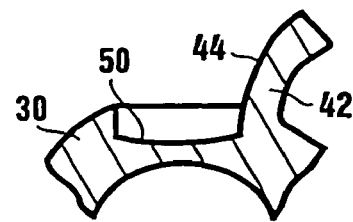
FIG. 6B is a cross-sectional view of a cornea as in FIG. 6A showing the cornea after the incision and lifting of a flap having a convex interior surface.

FIGS. 6A and 6B show an example of a flap 42 that can be cut using the methods of the present invention to create a prescribed lentoid 36 having a concave anterior surface 38. As discussed above, the versatility of the pulsed laser beam 12, alone or in combination with an excimer laser beam 13, enables one skilled in the art to create a flap 42 in accordance with the present invention which will result in a lentoid 36 having a plane, concave, convex or irregularly shaped anterior surface 38, and a plane, concave, convex or irregularly shaped posterior surface 40.

Figure 7:
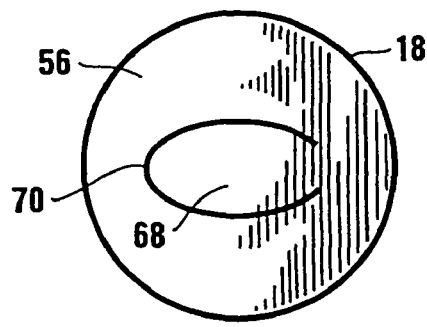
FIG. 7 is a plan view of a cornea after the incision of an oval flap.
Figure 8:
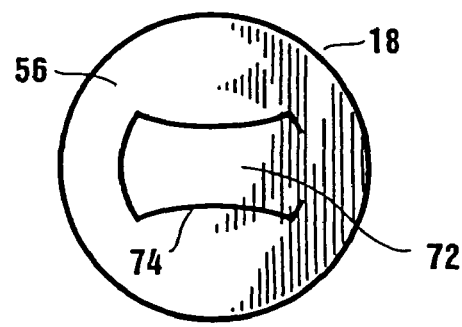
FIG. 8 is a plan view of a cornea after the incision of an elongated flap.

Further, as shown in FIG. 7, using the methods of the present invention, an oval flap 68 can be created having an oval anterior border 70. One benefit of the oval shape for flap 68 is that the oval shape allows for a bed 50 with a large exposed bed area. Similarly, as shown in FIG. 8, an elongated flap 72, having an elongated anterior border 74 can be created with the methods of the present invention. An elongated flap 72 may also provide the benefit of exposing a bed 50 with a large exposed bed area.

Figure 9:
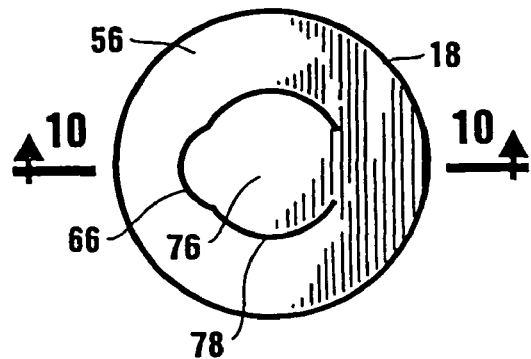
FIG. 9 is a plan view of a cornea after the incision of a flap having a tab.
Figure 10A:
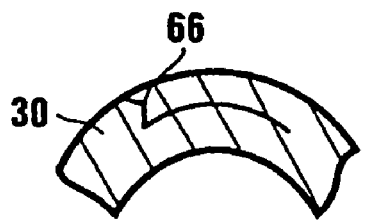
FIG. 10A is a cross-sectional view of a cornea as seen along the line 10-10 in FIG. 9, showing a flap having an integral tab to assist in lifting and repositioning the flap.
Figure 10B:
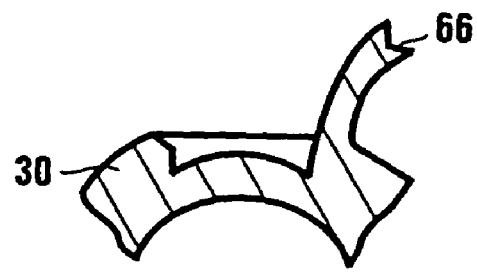
FIG. 10B is a cross-sectional view of a cornea as in FIG. 10a, showing the cornea after the incision and lifting of a flap having a tab.

Additionally, custom shaped flaps 76 can be created using the methods of the present invention. For example, as shown by cross-referencing FIGS. 9 and 10A-B, a custom flap 76 having a tab 66 can be made. Referring to FIG. 9, the tab 66 may have a different curvature than the custom anterior border 78 of the flap 76, and hence the tab 66 extends from the custom anterior border 78 to assist in lifting and repositioning the custom flap 76.

Figure 11:
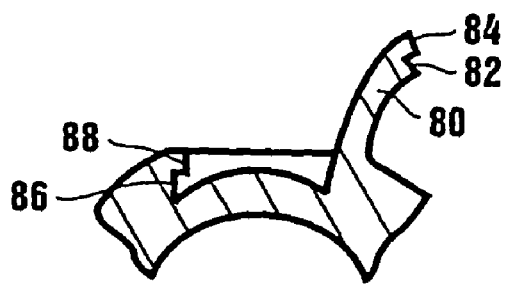
FIG. 11 is a plan view of a cornea after the incision of a flap having an interlocking feature.

In accordance with the methods of the present invention, an interlocking flap 80 as shown in FIG. 11 can be created for the purposes of maintaining the flap 80 in place after repositioning to both facilitate healing and reduce any optical distortions that may occur if a repositioned flap 42 shifts before healing is completed. As shown in FIG. 11, the interlocking flap 80 contains an interlocking peripheral edge 82. In one embodiment of the interlocking peripheral edge 82, an annular ring 84 extends from the interlocking peripheral edge 82 for engagement with a corresponding recess 86 formed in the wall 88.

Figure 12:
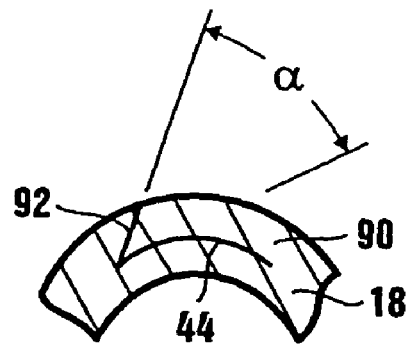
FIG. 12 is a plan view of a cornea after the incision of a flap having a beveled peripheral edge with an acute angle between the peripheral edge and the interior surface of the flap.

FIG. 12 shows an alternative embodiment of an interlocking flap 90, having a beveled peripheral edge 92 for interlocking of the flap 90 with the remaining cornea 18 after repositioning. In the embodiment shown in FIG. 12, the flap 90 is formed with the angle α between the beveled peripheral edge 92 and the interior surface 44 of the flap 90 as an acute angle. A flap 90 with a beveled peripheral edge 92 as shown in FIG. 12 is further disclosed in co-pending and now-allowed application Ser. No. 08/725,070 entitled "Method for Corneal Laser Surgery," which is incorporated herein by reference.

While the particular Method of Corneal Reshaping by Laser Incising a Contoured Corneal Flap as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A method of accessing a corneal tissue posterior to an anterior surface of a cornea, the method comprising:
    defining a first periphery at an anterior surface oft-he a cornea, the first periphery bounding a first cross-sectional area;
    defining a second periphery within stromal tissue of the cornea, the second periphery bounding a second cross-sectional area, wherein the second cross-sectional area is larger sized than the first cross-sectional area;
    incising stromal tissue so as to define a stromal tissue bed surface and a corresponding interior surface of a stromal tissue layer disposed anterior of the bed, the layer being radially outwardly bounded by the second periphery; and
        incising stromal tissue between substantial portions of the first periphery and the second periphery so as to define a peripheral edge of the layer and a corresponding peripheral wall of stromal tissue disposed radially outwardly of the peripheral edge of the layer, and such that at least some corneal tissue disposed within the peripheral edge remains radially connected to corneal tissue outside of the first and second peripheries, wherein the larger cross-sectional area of the second periphery induces interlocking engagement of the peripheral edge of the lager under the peripheral wall when the interior surface of the layer engages the bed.

2. The method of claim 1, wherein incising the layer of stromal tissue includes incising a concave, convex, or irregularly shaped surface stromal tissue.

3. The method of claim 1, wherein the first periphery comprises an elongate or oval shape.

4. The method of claim 1, wherein the second periphery comprises an elongate or oval shape.

5. The method of claim 1, wherein each incising step is performed using a pulsed laser.

6. The method of claim 1, wherein incising the layer and incising the peripheral edge together define a corneal flap, wherein the corneal flap comprises a hinge defined by the radially connected corneal tissue within the peripheral edge; the method further comprising:
    lifting the corneal flap by rotating the corneal flap about the hinge to expose the bed and photoaltering the exposed bed.

7. The method of claim 6, wherein the laser beam is used to photoalter the bed.

8. The method of claim 6, wherein photoaltering the bed comprises using an excimer laser beam to photoablate the bed.

9. The method of claim 6, further comprising repositioning the flap so that the interior surface engages the photoaltered bend and interlocking the peripheral edge under the peripheral wall so as to inhibit dislodging of the flap.

10. The method of claim 6, wherein the corneal flap defines an acute angle between the interior surface and the peripheral edge.

11. The method of claim 6, wherein the peripheral edge comprises an annular ring protruding radially outwardly posterior to the peripheral wall so as to interlock under a corresponding portion of the peripheral wall.

12. The method of claim 6, wherein the flap peripheral edge comprises a v-shaped edge.

13. A method of accessing a corneal tissue posterior to an anterior surface of a cornea, the method comprising:
    defining a first periphery at the anterior surface of the cornea, the first periphery bounding a first cross-sectional area;
    defining a second periphery within stromal tissue of the cornea, the second periphery bounding a second cross-sectional area, wherein the second cross-sectional area is sized differently than the first cross-sectional area and;
    incising a layer of stromal tissue using a pulsed laser, the layer being bounded by the second periphery and being non-planar; and
    incising stromal tissue between substantial portions of the first periphery and the second periphery using the a pulsed laser so as to define a peripheral edge radially bordering the layer and a peripheral wall disposed radially outwardly of the peripheral edge, the incised stromal tissue being along a non-linear path between the first and second peripheries, such that at least some corneal tissue disposed between the first and second peripheries remains connected to corneal tissue outside of the first and second peripheries, and such that a portion of the peripheral edge interlocks under a portion of the peripheral wall.

14. The method of claim 13, wherein the first periphery comprises an elongate or oval shape.

15. The method of claim 13, wherein the second periphery comprises an elongate or oval shape.

* * * * *